(12) United States Patent
Koresawa et al.

(10) Patent No.: US 7,112,706 B2
(45) Date of Patent: *Sep. 26, 2006

(54) DIMERDIOL DERIVATIVES AND COMPOSITION OF MATTER INCLUDING THE DIMERDIOL DERIVATIVES

(75) Inventors: Takeshi Koresawa, Shiga (JP); Yasuhiro Shiren, Shiga (JP); Isamu Noda, Shiga (JP); Hiroyuki Tanabe, Shiga (JP); Mie Noda, Shiga (JP); Akio Otera, Shiga (JP)

(73) Assignee: Croda Japan KK, Osaka (JP)

( * ) Notice: Subject to any disclaimer, the term of this patent is extended or adjusted under 35 U.S.C. 154(b) by 410 days.

This patent is subject to a terminal disclaimer.

(21) Appl. No.: 10/402,542

(22) Filed: Mar. 28, 2003

(65) Prior Publication Data

US 2003/0225223 A1 Dec. 4, 2003

(30) Foreign Application Priority Data

Apr. 24, 2002 (JP) .............................. 2002-121664

(51) Int. Cl.
*C07C 29/00* (2006.01)
(52) U.S. Cl. ..................................................... 568/840
(58) Field of Classification Search ................ 568/670, 568/840
See application file for complete search history.

(56) References Cited

U.S. PATENT DOCUMENTS

| | | | | | |
|---|---|---|---|---|---|
| 4,061,869 | A | * | 12/1977 | Schwarze et al. | ........... 524/377 |
| 4,670,580 | A | * | 6/1987 | Maurer | ........................ 560/89 |
| 5,977,404 | A | * | 11/1999 | Kwetkat et al. | ............... 562/36 |
| 6,075,065 | A | * | 6/2000 | Yamazaki et al. | ............. 522/64 |
| 6,252,037 | B1 | * | 6/2001 | Kojima et al. | ............... 528/300 |
| 6,312,513 | B1 | | 11/2001 | Hoefer et al. | ................ 106/499 |
| 2002/0064617 | A1 | * | 5/2002 | Tai et al. | .................... 428/36.6 |

FOREIGN PATENT DOCUMENTS

| | | | | |
|---|---|---|---|---|
| JP | 09136935 | A | * | 5/1997 |
| JP | 11061646 | A | * | 3/1999 |
| JP | 11302354 | A | * | 11/1999 |
| JP | 11302363 | A | * | 11/1999 |
| JP | 2000170032 | A | * | 6/2000 |
| JP | AA 2001-5072530 | | | 3/2001 |
| WO | WO96/30490 | | | 10/1996 |
| WO | WO98/08888 | | | 3/1998 |

* cited by examiner

*Primary Examiner*—Samuel Barts
*Assistant Examiner*—Kellette Gale
(74) *Attorney, Agent, or Firm*—Brown & Michaels, PC

(57) ABSTRACT

It is an object of the present invention to provide a dimer diol derivative and a composition containing the dimer diol derivative which have an excellent water-holding property, an excellent pigment dispersion property and further a high level of safety.

The dimer diol derivatives according to the present invention is a dimer diol derivative represented by the following chemical formula 19.

(chemical formula 19)

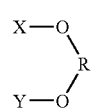

(wherein R is a dimer diol residue, X is hydrogen atoms, the following chemical formula 20 or the following chemical formula 21, and Y is hydrogen atoms, the following chemical formula 20 or the following chemical formula 21 (except that a case where both X and Y are hydrogen atoms), (chemical formula 20)

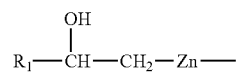

(wherein $R_1$ is an aliphatic hydrocarbon group having 1 to 22 carbon atoms, Z is the following chemical formula 22 and/or the following chemical formula 23, and n is an integer including zero), (chemical formula 21)

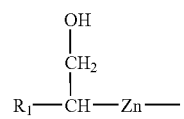

(wherein $R_1$ is an aliphatic hydrocarbon group having 1 to 22 carbon atoms, Z is the following chemical formula 22 and/or the following chemical formula 23, and n is an integer including zero), (chemical formula 22)

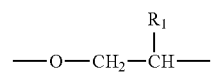

(wherein $R_1$ is an aliphatic hydrocarbon group having 1 to 22 carbon atoms), (chemical formula 23)

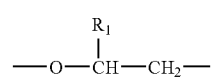

(wherein $R_1$ is an aliphatic hydrocarbon group having 1 to 22 carbon atoms).

9 Claims, 4 Drawing Sheets

DIMERDIOL DERIVATIVES AND COMPOSITION OF MATTER INCLUDING THE DIMERDIOL DERIVATIVES

BACKGROUND OF THE INVENTION

1. Field of the Invention

The present invention relates to a dimer diol derivative and a composition containing the dimer diol derivative, and it is an object of the present invention to provide a dimer diol derivative and a composition containing the dimer diol derivative which have an excellent water-holding property, an excellent pigment dispersion property and further a high level of safety.

2. Description of the Related Art

As materials for cosmetic, fats and oils, which are fatty acid triglyceride type, such as olive oil, palm oil, sesame oil, macadamia nut oil and mink oil or waxes such as lanolin are widely used.

Particularly, lanolin which is the ester of lanolin acid and lanolin alcohol has an excellent water-holding property and a high level of the emulsion stability and further an excellent emollient effect on the skin, it is widely used in not only emulsified products but also various makeup products and cosmetics for hairs.

However, fats and oils or waxes such as lanolin have the following problems.

Cosmetics formulated with fats and oils or waxes change over time to causes the dissociation of components and the deterioration of feeling in using when these are not adequately formulated. Further, since lanolin has a composition close to sebum and water-holding property, it has an excellent emollient effect on the skin. In recent years, however, there is a tendency of disliking animal materials from the viewpoint of the prevention of cruelty to animals. In addition, since lanolin is the ester of alcohol and fatty acid, it is of low stability and some of lanolin have decomposed and generated foul smells.

SUMMARY OF THE INVENTION

As a result of studying earnestly in consideration of the circumstances, the present inventors have found that a dimer diol derivative obtained by reacting dimer diol with epoxide has an excellent water-holding property, an excellent pigment dispersion property, and further a high level of safety and stability, thereby establishing the present invention.

DESCRIPTION OF THE PREFERRED EMBODIMENTS

Figure 1:
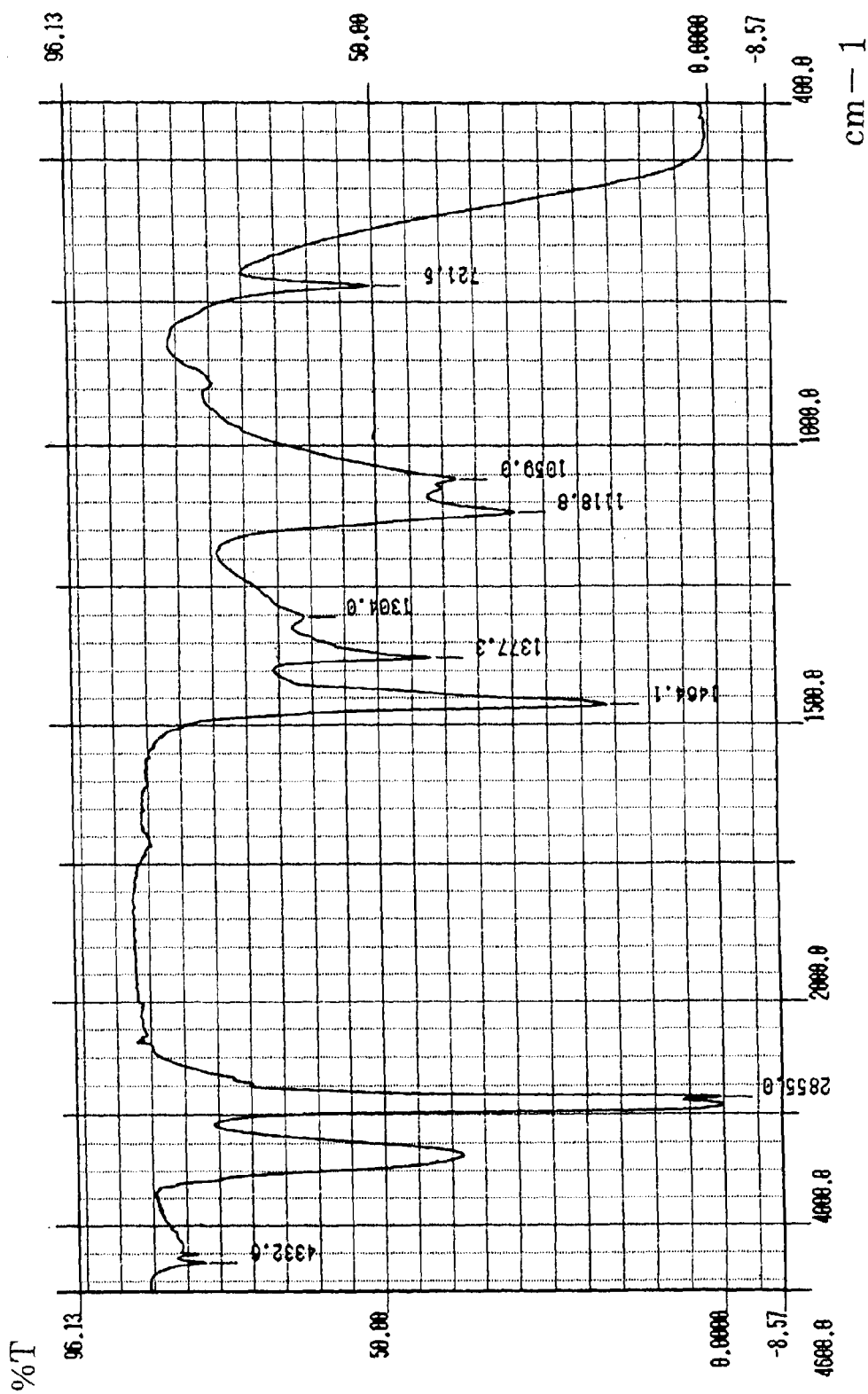
FIG. 1 is an infrared (IR) absorption spectrum chart on a test sample of Example 1.

Hereinafter, a dimer diol derivative and a composition containing the dimer diol derivative according to the present invention will be described.

The dimer diol derivative according to the present invention is represented by the following chemical formula 1.

(chemical formula 1)

(wherein R is a dimer diol residue, X is hydrogen atoms, the following chemical formula 2 or the following chemical formula 3, and Y is hydrogen atoms, the following chemical formula 2 or the following chemical formula 3 (except that a case where both X and Y are hydrogen atoms)

(chemical formula 2)

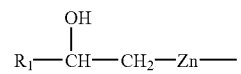

(wherein $R_1$ is an aliphatic hydrocarbon group having 1 to 22 carbon atoms, Z is the following chemical formula 4 and/or the following chemical formula 5, and n is an integer including zero)

(chemical formula 3)

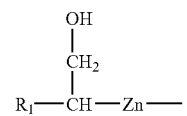

(wherein $R_1$ is an aliphatic hydrocarbon group having 1 to 22 carbon atoms, Z is the following chemical formula 4 and/or the following chemical formula 5, and n is an integer including zero)

(chemical formula 4)

(wherein $R_1$ is an aliphatic hydrocarbon group having 1 to 22 carbon atoms)

(chemical formula 5)

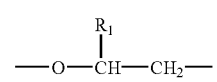

(wherein $R_1$ is an aliphatic hydrocarbon group having 1 to 22 carbon atoms)

In the above chemical formula 1, X and Y are hydrogen atoms, the following chemical formula 2 or the following chemical formula 3 (except that a case where both X and Y are hydrogen atoms).

In the above chemical formula 1, R is a dimer diol residue which is obtained by removing two hydroxyl groups from dimer diol and specifically represented by the following chemical formula 6 or the following chemical formula 7.

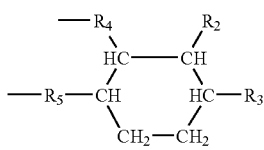

(chemical formula 6)

(wherein $R_2$ and $R_3$ are alkyl groups, $R_4$ and $R_5$ are alkylene groups, and the total number of carbon atoms of $R_2$, $R_3$, $R_4$ and $R_5$ is 14 to 42)

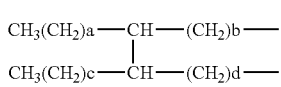

(chemical formula 7)

(wherein a, b, c and d are each integers and are within a range of a+b+c+d=16 to 44)

In addition, in the above chemical formula 6, $R_2$ and $R_3$ are alkyl groups, more specifically straight-chain alkyl groups. Examples thereof include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group and the like. $R_2$ and $R_3$ may be the same kind of alkyl groups as each other or may be different kind of alkyl groups.

In the above chemical formula 6, $R_4$, and $R_5$ are alkylene groups. Examples thereof include an ethylene group, a propylene group, a butylene group, a pentylene group, a hexylene group, a heptylene group, an octylene group, a nonylene group, a decylene group, an undecylene group, a dodecylene group, a tridecylene group, a tetradecylene group, a pentadecylene group, a hexadecylene group, a heptadecylene group, an octadecylene group, a nonadecylene group, an eicosylene group and the like. $R_4$ and $R_5$ may be the same kind of alkyl groups as each other or may be different kind of alkyl groups.

In the above chemical formula 6, the total number of carbon atoms of $R_2$, $R_3$, $R_4$ and $R_5$ is 14 to 42. Particularly in the present invention, the total number of carbon atoms is 18 to 40, preferably 30 to 40.

In the above chemical formula 7, a, b, c and d are each integers and satisfy the relationship: a+b+c+d=16 to 44. In the present invention, it is preferred to be a+b+c+d=18 to 40 and particularly preferred to be a+b+c+d=30 to 40.

In the above chemical formula 2, chemical formula 3, chemical formula 4 and chemical formula 5, $R_1$ is hydrogen atoms or an aliphatic hydrocarbon group having 1 to 22 carbon atoms. The aliphatic hydrocarbon group having 1 to 22 carbon atoms may be either a straight-chain aliphatic hydrocarbon group or a branched-chain aliphatic hydrocarbon group. Examples thereof include straight-chain or branched-chain alkyl groups, alkenyl groups, alkynyl groups and the like.

More specifically, examples thereof include: straight-chain saturated aliphatic hydrocarbon groups such as a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group and a behenyl group; branched-chain saturated aliphatic hydrocarbon groups such as an isopropyl group, an isobutyl group, a sec-butyl group, a tert-butyl group, an isopentyl group, a neopentyl group, an isostearyl group, an isoheptadecyl group and an isotridecyl group; straight-chain unsaturated aliphatic hydrocarbon groups such as an ethynyl group, a vynyl group, a provynyl group, a propenyl group, a geranyl, group, a linalyl group, a neryl group, an aryl group, a butenyl group, a hexenyl group, an octenyl group, a decenyl group and a hexadecenyl group; and branched-chain unsaturated aliphatic hydrocarbon groups such as an isopropenyl group and an isopropylidene group.

In the present invention, $R_1$ is preferably a straight-chain or a branched-chain saturated aliphatic hydrocarbon group having 6 to 22 carbon atoms, more preferably a straight-chain or a branched-chain saturated aliphatic hydrocarbon group having 10 to 18 carbon atoms. The reason for this is that when $R_1$ is a straight-chain or a branched-chain hydrocarbon group having carbon atoms being less than 6, the compatibility with other fats and oils in compositions becomes bad, and when the number of carbon atoms of $R_1$ exceeds 22, the affinity for the skins becomes inferior; therefore, both cases are not preferred.

In the above chemical formula 2 and chemical formula 3, Z is the above chemical formula 4 and/or the above chemical formula 5, and n is an integer.

Z may be constituted of only the above chemical formula 4 or constituted of only the above chemical formula 5, or further constituted of both the above chemical formulas 4 and 5. When it is constituted of both the above chemical formulas 4 and 5, the order of arrangement is not particularly limited and an optional order can be employed.

Further, n is an integer including zero, generally an integer equal to or less than 38, and preferably an integer equal to or less than 20.

Among the dimer diol derivatives according to the present invention, the most preferable derivative is a dimer diol derivative represented by the following chemical formula 8.

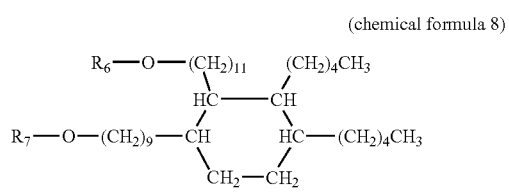

(chemical formula 8)

(wherein $R_6$ is hydrogen atoms, the following chemical formula 9 or the following chemical formula 10, and $R_7$ is hydrogen atoms, the following chemical formula 9 or the following chemical formula 10 (except that a case where both $R_6$ and $R_7$ are hydrogen atoms))

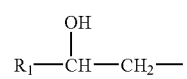

(chemical formula 9)

(wherein $R_1$ is an aliphatic hydrocarbon group having 1 to 22 carbon atoms)

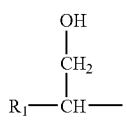

(chemical formula 10)

(wherein R$_1$ is an aliphatic hydrocarbon group having 1 to 22 carbon atoms)

The dimer diol derivative according to the present invention has an excellent water-holding property. The dimer diol derivative according to the present invention includes a part originated from dimer diol, and a part originated from a hydrocarbon group. The part originated from dimer diol tends to take a liquid crystal structure like lipid between corneas because of a rigid structure of molecules and has a high level of water-holding property (about not less than 200%). Further, the part originated from a hydrocarbon group has a structure which is similar to fatty acid of sebum and therefore a high affinity for the skins. Thus, the dimer diol derivative according to the present invention has the excellent water-holding property, and particularly when an alkyl group having a carbon chain length close to sebum is used in the part of hydrocarbon group, the dimer diol derivative having more excellent water-holding property can be obtained.

Further, since the dimer diol derivative according to the present invention is not one where fatty acid and lanolin alcohol are bonded by ester bond to form unlike lanolin and but one where the part originated from dimer diol and the part originated from a hydrocarbon group are bonded by ether bond being chemically highly stable, substance which has a high level of hydrolysis stability and a higher level of stability can be obtained.

Next, description will be given of an example of a process suitable for producing a dimer diol derivative according to the present invention. The dimer diol derivative according to the present invention can be obtained by reacting dimer diol with epoxide.

Dimer diol is diol which is obtained by reducing dimer acid. Though the number of carbon atoms of dimer diol is not particularly limited, the dimer diol has preferably 20 to 48 carbon atoms. Particularly in the present invention, there is preferably used the dimer diol having 36 carbon atoms obtained by reducing dimer of aliphatic unsaturated carboxylic acid having 18 carbon atoms.

Examples of the commercially available dimer diol include PRIPOL 2033 manufactured by Uniqema Japan, PESPOL HP-1000 manufactured by Toagosei Co., Ltd. and the like.

It is noted that dimer diol, which is obtained by hydrogenating dimer acid obtained by dimerizing aliphatic unsaturated carboxylic acid, contains mainly compounds represented by the chemical formula 11 and the chemical formula 12.

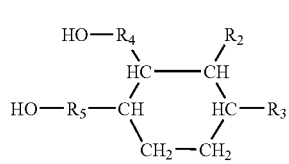

(chemical formula 11)

(wherein R$_2$ and R$_3$ are alkyl groups, R$_4$ and R$_5$ are alkylene groups, and the total number of carbon atoms of R$_2$, R$_3$, R$_4$ and R$_5$ is 14 to 42)

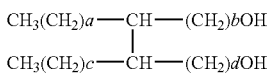

(chemical formula 12)

(wherein a, b, c and d are each integers and are within a range of a+b+c+d=16 to 44)

Although, epoxide is not particularly limited, 1,2-epoxyhexane, 1,2-epoxyoctane, 1,2-epoxydecane, 1,2-epoxytetradecane, 1,2-epoxydodecane, 1,2-epoxyhexadecane, 1,2-epoxyoctadecane, 1,2-epoxy-5-hexene, 1,2-epoxy-7-octene, 1,2-epoxy-9-decene, 1,2-epoxy-9-hexadecene and the like can be used, and one kind thereof can be alone used, and two or more kinds thereof can also be mixed to be used. Particularly in the present invention, it is preferred to use 1,2-epoxydodecane, 1,2-epoxytetradecane, 1,2-epoxyhexadecane and 1,2-epoxyoctadecane.

It is also possible to react dimer diol with epoxide dissolving them in a solvent or to react dimer diol with epoxide without a solvent in reaction between the above-mentioned dimer diol and epoxide. A solvent, which can be used, is not limited as long as the solvent does not contain alcohol and water. Example thereof include formamide, N,N-dimethyl formamide, N,N-dimethyl acetoamide, N-methyl-2-pyrrolidone, pyridine, dimethylsulfoxide, dioxane, tetrahydrofuran, dichloromethane, chloroform, carbon tetrachloride, 1,1-dichloroethane, 1,2-dichloroethane, benzene, toluene, xylene, dioxane and the like. Particularly in the present invention, it is preferred to use dimethylsulfoxide when a solvent is used.

The dimer diol and the epoxide are preferably charged in proportions of 1:0.5 to 40 by mol ratio, more preferably in proportions of 1:1 to 20. Molecular weights of the resulting dimer diol derivative can be optionally adjusted by changing a ratio of an amount of the dimer diol to that of the epoxide to be used.

Next, the dimer diol derivative according to the present invention can be obtained by reacting the dimer diol with epoxide under a temperature condition of 50 to 150° C., preferably under a temperature condition of 80 to 130° C.

Further, it is possible to add a catalyst when the above-mentioned dimer diol is reacted with the epoxide. Although usable catalyst is not limited, examples thereof include potassium hydroxide, sodium hydroxide, pyridine, triethyl amine, lithium hydroxide and the like.

When a catalyst is used, an amount of the catalyst used is not limited and 0.1 to 20% by weight of catalyst relative to the epoxide is used and 0.1 to 15% by weight is preferably used.

A raw dimer diol derivative obtained by removing the solvent after the above reaction is generally dilute brown and contains unreacted substances and solvents. It is possible to use the raw dimer diol derivative as formulating material as it is, but this is preferably refined. Examples of the method of refining include an acid treatment, an alkaline treatment, an activated carbon treatment, an activated clay treatment, vacuum steam deodorization or a method using these processes appropriately in combination, which have been conventionally used. Particularly in the present invention, it is preferred to use a refining process through column chromatography as described in Japanese Unexamined Patent Publication No. 62-205005. According to this method, the dimer diol derivative, which are white in color and smell-less, and highly stable without varying with time, can be obtained.

A composition according to the present invention can be obtained by mixing various ingredients used in ordinary cosmetics, pharmaceuticals and quasi-drugs appropriately and optionally into the dimer diol derivative according to the present invention.

Examples of the various ingredients to be mixed include fats and oils, waxes, hydrocarbons, higher fatty acids, higher alcohols, sterols, fatty esters, surfactants, high polymers, pigments, dyes and the like.

Specifically, examples of the fats and oils include avocado oil, almond oil, olive oil, cocoa butter, tallow, sesame oil, wheat germ oil, safflower oil, shea butter, turtle oil, camellia oil, bersic oil, castor oil, grape oil, macadamia nut oil, mink oil, york oil, rhus succedanea fruit wax, palm oil, hydrogenated oil and the like.

Examples of the waxes include orange roughy oil, carnauba wax, candelilla wax, spermaceti, jojoba oil, montan wax, beeswax, lanolin and the like.

Examples of the hydrocarbons include liquid paraffin, Vaseline (trademark), paraffin, ceresin, microcrystalline wax, squalane and the like.

Examples of the higher fatty acids include lauric acid, myristic acid, palmitic acid, stearic acid, oleic acid, behenic acid, undecylenic acid, oxystearic acid, linoleic acid, lanolin acid, synthetic fatty acid and the like.

Examples of the higher alcohols include lauryl alcohol, cetyl alcohol, cetostearyl alcohol, stearyl alcohol, oleyl alcohol, behenyl alcohol, lanolin alcohol, hydrogenated lanolin alcohol, hexyldecanol, octyldodecanol, isostearyl alcohol and the like.

Examples of the sterols include cholesterol, dihydrocholesterol, phytosterol and the like. Examples of the fatty esters include ethyl linoleate, isopropyl myristate, isopropyl lanolate, hexyl laurate, myristyl myristate, cetyl myristate, octyldodecyl myristate, decyl oleate, octyldodecyl oleate, hexyldecyl dimethyl octanoate, cetyl isooctanoate, cetyl palmitate, glycerin trimyristate, caprylic/capric triglycerin, propylene glycol dioleate, glycerin triisostearate, glycerin triisostearate, cetyl lactate, myristyl lactate, diisostearyl malate, cholesteryl stearate, cholesteryl isostearate, cholesteryl 12-hydroxystearate and the like.

Examples of the water-holding materials include glycerin, propylene glycol, 1,3-butylene glycol, polyethylene glycol, sodium lactate, sorbitol, sodium hyaluronate and the like.

Examples of the surfactants include an anionic surfactant, a cationic surfactant, an amphoteric surfactant, a nonionic surfactant and the like.

Examples of the high polymers include: natural high polymers such as arabic gum, tragacanth gum, guar gum, locust bean gum, sterculia urens gum, iris moss, quince seed, gelatin, shellac, rosin and casein; semi-synthetic high polymers such as carboxymethyl cellulose, hydroxymethyl cellulose, methyl cellulose, ethyl cellulose, sodium alginate, ester gum, hydroxypropyl cellulose and crystalline cellulose; and synthetic high polymers such as polyvinyl alcohol, polyvinyl pyrrolidone, sodium polyacrylate, carboxyvinyl polymer, polyvinyl methyl ether, polyamide resin and silicone oil.

Examples of the pigments include: colored pigments such as iron oxide, ultramarine blue, iron blue, chromium oxide, chromium hydrooxide, carbon black and manganese violet; white pigments such as titanium oxide and zinc oxide; and extender such as talc, mica, calcium carbonate and magnesium carbonate.

Examples of the dyes include tar pigments such as azo-based pigments, nitro-based pigments, nitroso-based pigments, xanthene-based pigments, quinoline-based pigments, anthraquinone-based pigments, indigo-based pigments and triphenylmethane-based pigments.

In addition to these, skin astringents such as citric acid, tartaric acid, lactic acid, aluminum chloride, aluminum sulfate, potassium sulfate, zinc sulfate, perfume, preservatives, germicides, anti-oxidant, ultraviolet absorber, hormones, vitamins, amino acid, hair restoration agents, whitening agents, extracts of animal and plant, water, ethanol, propanol and the like can be formulated appropriately and optionally.

The composition according to the present invention can be prepared into the compositions of various forms such as liquid form, solid form and paste form. Specifically, examples thereof include: fundamental cosmetics such as wash, emulsion, lotion, cream, cosmetic liquid, oil, pack and lip cream; makeup cosmetics such as foundation, lipstick, blusher, eye shadow, eye liner, mascara and eye blow liner; and cosmetics for hairs such as hair cream, hair conditioner, hair treatment, hair wax, tonic and hair liquid.

The content of the dimer diol derivative in the composition according to the present invention can be appropriately and optionally adjusted into the content corresponding to the form of the composition and usually 0.001 to 100% by weight, preferably 0.01 to 70% by weight is used.

It is noted that the composition according to the present invention may be included in any one of cosmetics, quasi-drugs and pharmaceuticals defined by Pharmaceutical Affairs Law and even when the composition is not included therein, it includes all ones used for external application to the human body.

EXAMPLES

Hereinafter, the present invention will be described on the basis of examples; however, the present invention is not limited to these examples.

Preparation of Test Sample of Example 1

102.5 g (0.18 mol) of dimer diol (trade name: PRIPOL 2033, manufactured by Uniqema Japan Co., Ltd.) having 36 carbon atoms and 35.3 g (0.18 mol) of a mixture of straight-chain epoxyalkane (trade name: AOE-X24, manufactured by Daicel Chemical Industries Co., Ltd.) having 12 carbon atoms and epoxyalkane having 14 carbon atoms were charged into a 500 mL of four necked flask, 5.3 g of potassium hydroxide was added as a catalyst, and this mixture was reacted at 105° C. for three hours. After reaction, the catalyst was neutralized, the content was dissolved with methyl isobutyl ketone and then washed with water, and methyl isobutyl ketone was recovered. Then, 125.2 g of a dimer diol derivative represented by the following chemical formula 13 was obtained by completely removing the methyl isobutyl ketone through the steam distillation.

Preparation of Test Sample of Example 2

157.3 g of a dimer diol derivative represented by the following chemical formula 13 was obtained by the procedures similar to those of the preparing method of Example 1 except for changing the charge ratio between the dimer diol and the straight-chain epoxyalkanes having 12 and 14 carbon atoms to 1:2 (mol ratio).

Preparation of Test Sample of Example 3

285.6 g of a dimer diol derivative represented by the following chemical formula 15 was obtained by the procedures similar to those of the preparing method of Example 1 except for changing the charge ratio between the dimer diol and the straight-chain epoxyalkanes having 12 and 14 carbon atoms to 1:6 (mol ratio).

(chemical formula 13)

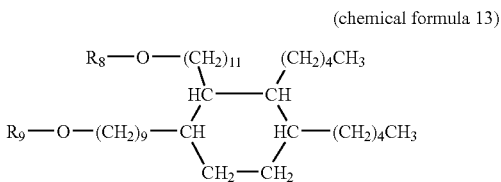

(wherein $R_8$ and $R_9$ are hydrogen atoms or the following chemical formula 14 (except that a case where both $R_8$ and $R_9$ are hydrogen atoms))

(chemical formula 14)

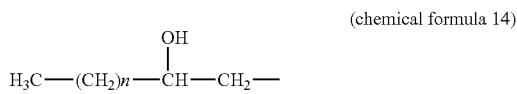

(wherein n is 9 or 11)

(chemical formula 15)

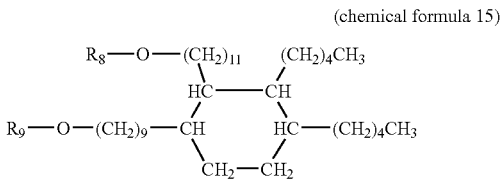

(wherein $R_8$ and $R_9$ are hydrogen atoms or the following chemical formula 16 (except that a case where both $R_8$ and $R_9$ are hydrogen atoms))

(chemical formula 16)

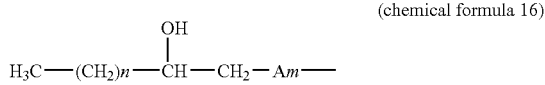

(wherein n is 9 or 11, A is the following chemical formula 17 and/or the following chemical formula 18, and m is 0 to 5)

(chemical formula 17)

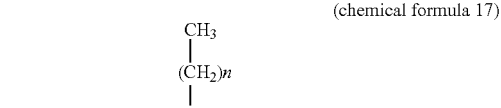

(wherein n is 9 or 11)

(chemical formula 18)

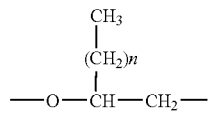

(wherein n is 9 or 11)

Test Example 1

Infrared (IR) Absorption Spectroscopy Analysis

Figure 2:
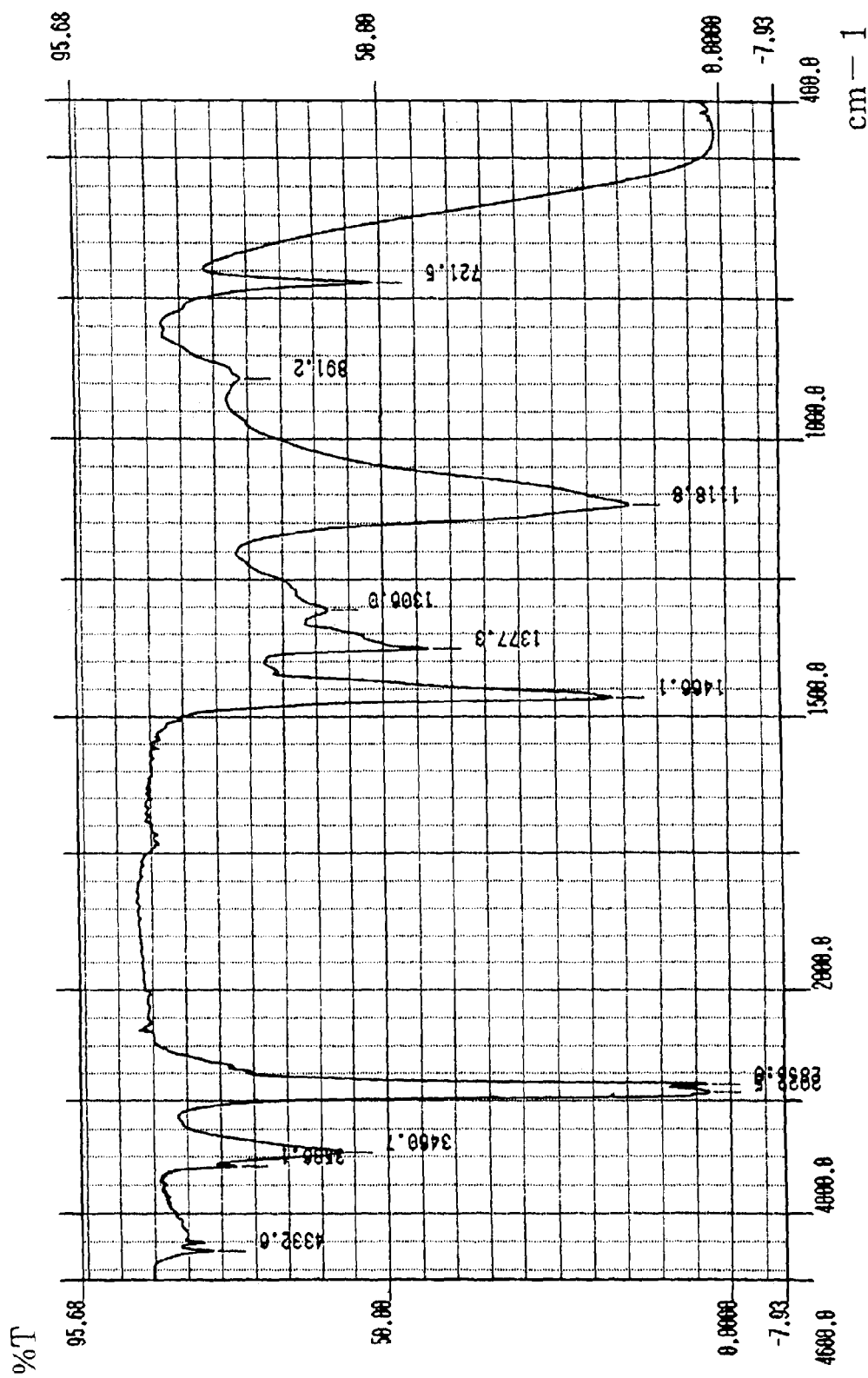
FIG. 2 is an infrared (IR) absorption spectrum chart on a test sample of Example 3.

IR analyses were performed on the test samples of Examples 1 and 3 prepared as described above. Measurements thereof are shown in FIGS. 1 and 2. As shown in FIGS. 1 and 2, there was recognized absorption originated from an ether bond in the vicinity of 1118.8 cm$^{-1}$.

Figure 3:
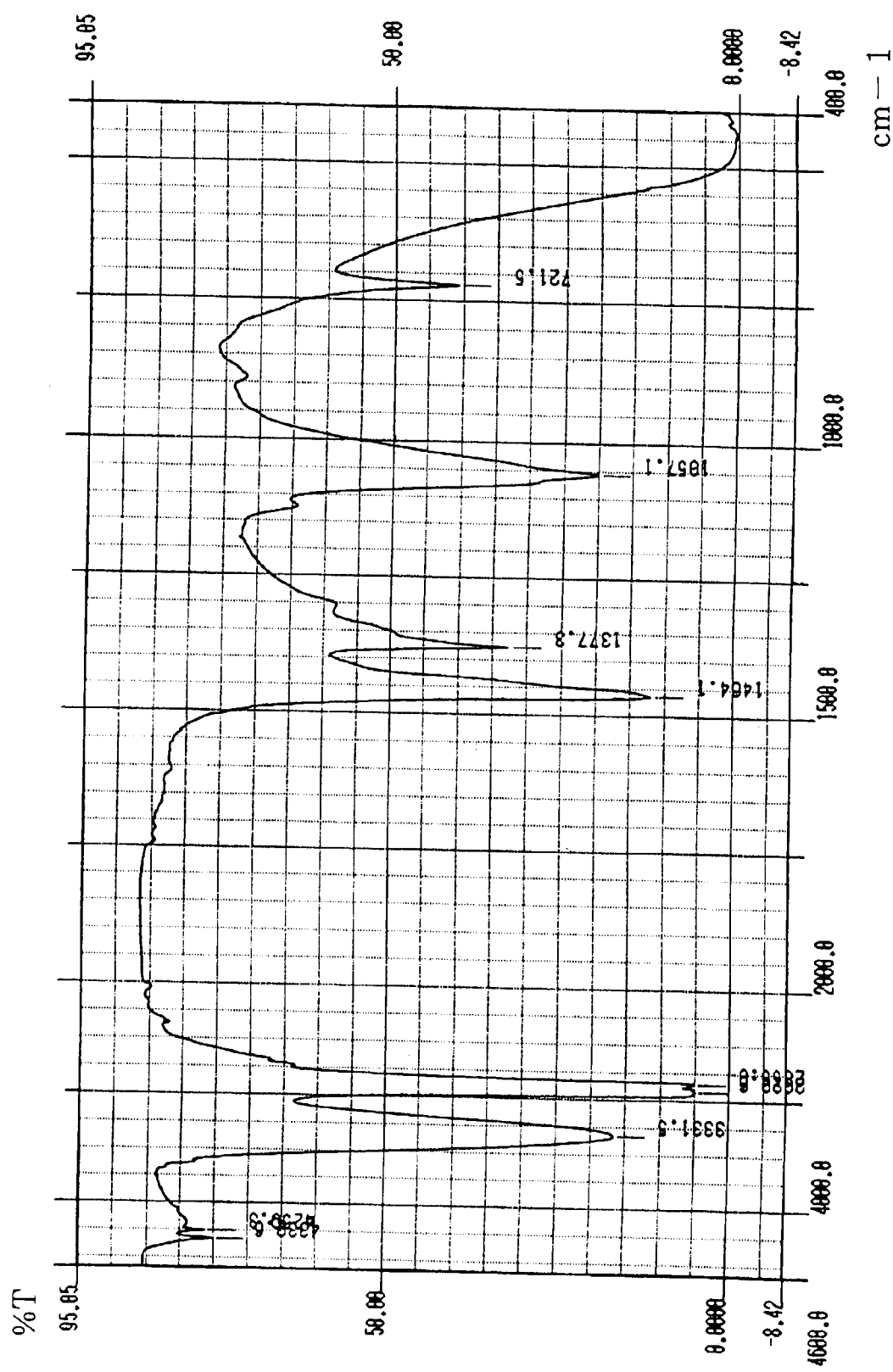
FIG. 3 is an infrared (IR) absorption spectrum chart on dimer diol used in preparation of test samples of examples.
Figure 4:
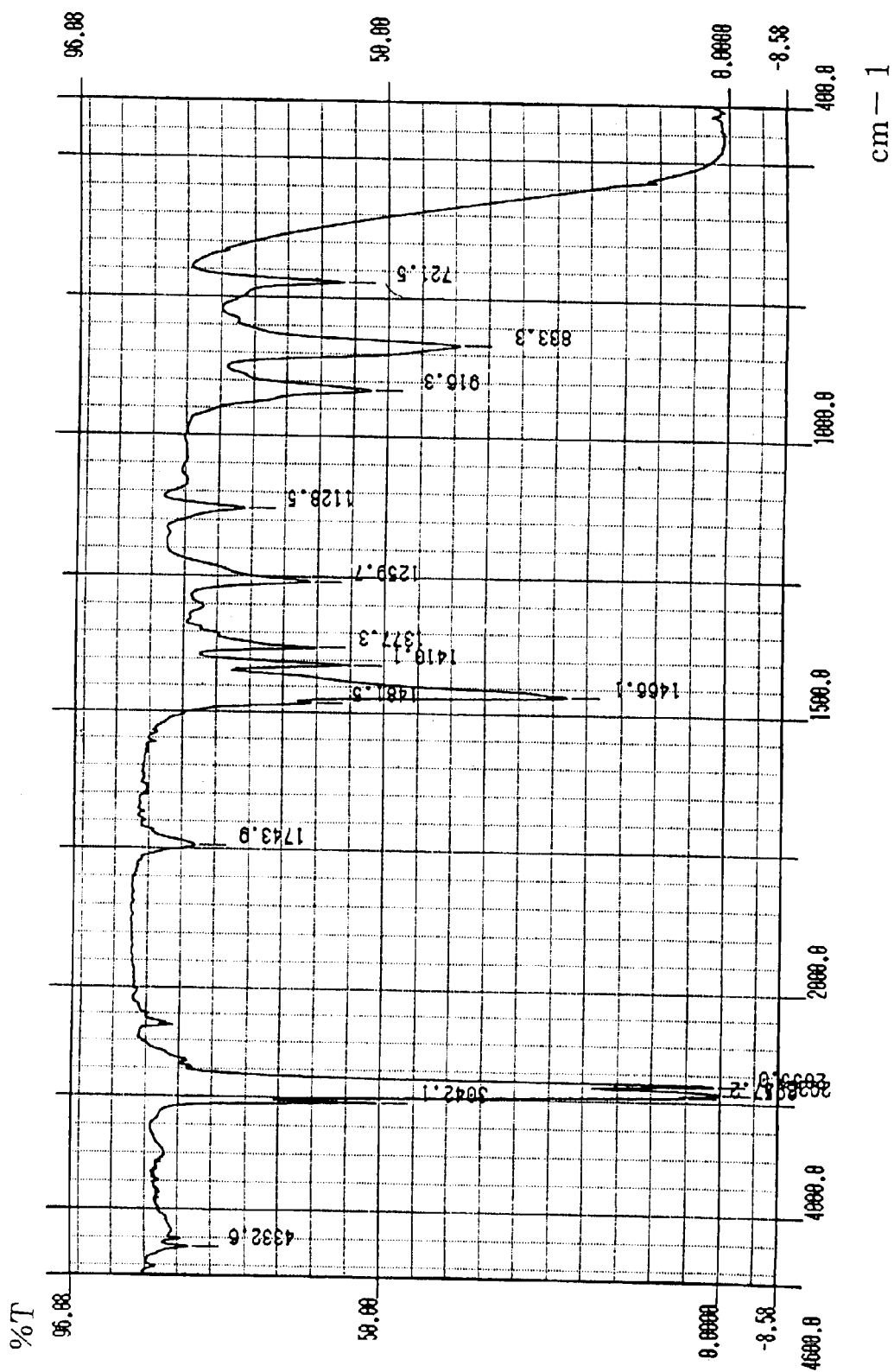
FIG. 4 is an infrared (IR) absorption spectrum chart on epoxy alkane used in preparation of test samples of examples.

It is noted that FIG. 3 shows the IR absorption spectroscopy charts of dimer diols used for preparation of test samples of examples, and FIG. 4 shows the IR absorption spectroscopy charts of epoxyalkanes used for preparation of test samples of examples.

Test Example 2

Water-Holding Property Measurement

Water-holding property was measured on the test samples of Examples 1 to 3 prepared as described above and lanolin. In measuring, 10 g of each of the test samples were put in a mortar at room temperature, the samples were kneaded while dripping pure water little by little, and the maxim amount of pure water added, in which samples can be mixed without separating into two phases, was determined. Measurements are shown in Table 1. It is noted that the values in Table 1 are represented by a weight ratio of samples and water added thereto.

TABLE 1

| | Example 1 | Example 2 | Example 3 | Lanolin |
|---|---|---|---|---|
| Water-holding property (%) | 375 | 285 | 201 | 300 |

As shown in Table 1, it is understood that the dimer diol derivative according to the present invention has the water-holding property which is equal to or more than that of lanolin known to be excellent in the water-holding property.

Test Example 3

Pigment Dispersion Property

The pigment dispersion property was measured on the test samples of Examples 1 to 3 prepared as described above and liquid lanolin. In measuring, the respective test samples were diluted to 5% by weight with liquid paraffin. The diluted samples were kneaded while being dripped onto 10 g of titanium oxide placed in a mortar little by little, and an amount of the samples dripped at the moment when the titanium oxide becomes wholly wet (wet point) and an amount of the samples dripped at the moment when the titanium oxide starts to flow out (fluidizing point) are determined and these amounts were respectively converted to the amount per 100 g titanium oxide. It is noted that the less the difference between a fluidizing point and a wet point, the better the pigment dispersion property becomes. Measurements are shown in Table 2.

TABLE 2

|  | Example 1 | Example 2 | Example 3 | Liquid lanolin |
|---|---|---|---|---|
| Pigment dispersion property (fluidizing point-wet point) (g/100 g TiO$_2$) | 31 | 34 | 30 | 55 |

As shown in Table 2, it is understood that the dimer diol derivative according to the present invention has the considerably excellent pigment dispersion property in comparison with liquid lanolin known to be excellent in the pigment dispersion property.

Preparation of Test Samples of Examples 4 to 6 and Comparative Examples 1 to 3

Test samples (emulsion) of Examples 4 to 6 and Comparative Examples 1 to 3 were prepared in accordance with the formulas in Table 3.

TABLE 3

|  | Example 4 | Example 5 | Example 6 | Comparative Example 1 | Comparative Example 2 | Comparative Example 3 |
|---|---|---|---|---|---|---|
| Squalane | 4.5 | 4.5 | 4.5 | 4.5 | 4.5 | 4.5 |
| Hydrogenated soybean phospholipid | 0.5 | 0.5 | 0.5 | 0.5 | 0.5 | 0.5 |
| Test sample of Example 1 | 3.6 | — | — | — | — | — |
| Test sample of Example 2 | — | 3.6 | — | — | — | — |
| Test sample of Example 3 | — | — | 3.6 | — | — | — |
| Olive oil | — | — | — | 3.6 | — | — |
| Palm oil | — | — | — | — | 3.6 | — |
| Refined lanolin | — | — | — | — | — | 3.6 |
| Vitamin E | 0.05 | 0.05 | 0.05 | 0.05 | 0.05 | 0.05 |
| Propylparaben | 0.1 | 0.1 | 0.1 | 0.1 | 0.1 | 0.1 |
| Glycerin | 8.5 | 8.5 | 8.5 | 8.5 | 8.5 | 8.5 |
| Maltitol ester laurate | 1.2 | 1.2 | 1.2 | 1.2 | 1.2 | 1.2 |
| Methylparaben | 0.1 | 0.1 | 0.1 | 0.1 | 0.1 | 0.1 |
| Disodium edetate | 0.05 | 0.05 | 0.05 | 0.05 | 0.05 | 0.05 |
| Purified water | 81.02 | 81.02 | 81.02 | 81.02 | 81.02 | 81.02 |
| Carboxyvinyl polmer | 0.3 | 0.3 | 0.3 | 0.3 | 0.3 | 0.3 |
| Sodium hydroxide | 0.08 | 0.08 | 0.08 | 0.08 | 0.08 | 0.08 |
| Total | 100 | 100 | 100 | 100 | 100 | 100 |

Test Example 4

Tests of Stability and Application Feelings

The stability and application feelings were tested using the respective test samples of Examples 4 to 6 and Comparative Examples 1 to 3 prepared as described above.

The stability was evaluated through observing the appearances after leaving the samples at 40° C. for 30 days. In addition, application feelings were evaluated by 10 panels in accordance with the following criteria, and the average ratings were taken as the application feelings of each test sample. Results are shown in Table 4.

Evaluation Criteria: Moist Feeling
5: highly moist
4: moist
3: ordinary
2: not moist
1: not moist at all

TABLE 4

|  | Example 4 | Example 5 | Example 6 | Comparative example 1 | Comparative example 2 | Comparative example 3 |
|---|---|---|---|---|---|---|
| Stability | Stable | Stable | Stable | Separated | Separated | Stable |
| Moist feeling | 5 | 5 | 5 | 3 | 2 | 5 |

As shown in Table 4, the test samples of Examples 4 to 6 were very stable without separating after 30 days elapsed. Further, these samples were moist and had excellent application feelings. It is understood from these results that the dimer diol derivative according to the present invention is excellent in the application feelings and the stability in comparison with ones mixed with the olive oil or the palm oil.

Hereinafter, there is shown examples of formulas of compositions according to the present invention. An amount of formulation is represented by weight percent.

Formulation 1

Emollient Cream

| A | |
|---|---|
| Glyceryl monostearate | 3.00 |
| Polyglyceryl monoisostearate | 0.50 |
| Sorbitan monostearate | 1.20 |
| Myristyl alcohol | 2.00 |
| Test sample of Example 1 | 6.00 |
| Medofoam oil | 25.05 |
| Hydrogenated soybean phospholipid | 0.50 |
| Tocopherol | 0.05 |
| Propylparaben | 0.15 |
| B | |
| Glycerin | 14.00 |
| Methylparaben | 0.25 |
| Purified water | 32.20 |
| C | |
| 2% carboxyvinyl polymer dispersion liquid | 13.00 |
| D | |
| Purified water | 2.00 |
| Sodium hydroxide | 0.10 |
| Total | 100.00 |

After A and B are weighed, these are homogeneously dissolved respectively at 80° C. A is added to B, and the mixture is agitated with an anchor mixer and a homo mixer (5000 rpm) and emulsified. After emulsification, mixing is switched to an agitation of low speed, and C is added to the emulsion and the mixture is agitated until it becomes homogeneous. After homogenizing, the mixture is added with D and agitated. When the mixture becomes homogeneous, the homo mixer is stopped and the mixture is cooled to a temperature of 30° C. or less and simultaneously vacuum deaerated while agitating with the anchor mixer.

Formulation 2

Liquid Foundation

| Oil Phase | |
|---|---|
| Cyclic silicone oil | 5.00 |
| Polyether modified silicone oil | 15.00 |
| Beeswax | 1.20 |
| Polyoxyethylene stearyl ether (2EO) | 0.50 |
| OctyldimethylPABA | 2.00 |
| Test sample of Example 1 | 8.00 |
| Propylparaben | 0.15 |
| Phenoxyethanol | 0.15 |
| Color powder | 14.50 |

-continued

| Water Phase | |
|---|---|
| Propylene glycol | 8.00 |
| Sodium chloride | 2.00 |
| Purified water | 43.00 |
| Sodium dehydroacetate | 0.30 |
| Trisodium edetate | 0.10 |
| Glycyrrhizinate dipotassium | 0.10 |
| Total | 100.00 |
| Color Powder | |
| 20% silicone-treated titanium oxide | 64.58 |
| 20% silicone-treated talc | 25.54 |
| 20% silicone-treated yellow iron oxide | 7.43 |
| 20% silicone-treated iron oxide (trade name "SI-2 TAROX R-516L" manufactured by Daito Chemical Co., Ltd.) | 0.41 |
| 20% silicone-treated iron oxide (trade name "S1-2 BENGARA No. 217" manufactured by Daito Chemical Co., Ltd.) | 1.15 |
| 20% silicone-treated black iron oxide | 0.89 |
| Total | 100.00 |

An oil phase is heated to and dissolved at 80 to 90° C., and after the oil phase dissolves completely, it is cooled to a temperature of 50° C. and then added with water phase of the same temperature, and the mixture is emulsified with a homodisper. Then, color powder is gradually added to and dispersed into the emulsion while agitating. After the dispersion of the powder, the mixture is cooled to a temperature of 30° C. or less while agitating. After cooling, the mixture is deaerated and filled.

Formulation 3

Treatment

| A | |
|---|---|
| Incrocwat behenyl TMS (behentrimonium methosufate + cetostearyl alcohol) | 6.00 |
| Test sample of Example 1 | 8.00 |
| Methylparaben | 0.10 |
| Propylparaben | 0.10 |
| B | |
| Purified water | 85.60 |
| Sodium benzoate | 0.20 |
| Total | 100.00 |

After A and B are weighed, these are homogeneously dissolved respectively at 80 to 90° C. The mixture is agitated with a homo mixer (3000 to 5000 rpm) and emulsified while B is gradually added to A. After emulsification, the mixture is cooled to a temperature of 25° C. or less with cooling water.

What is claimed is:

1. A dimer diol derivative represented by the following chemical formula 19, (chemical formula 19)

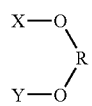

(wherein:
R is the following chemical formula 6 or the following chemical formula 7,
X is a hydrogen atom, the following chemical formula 20, or the following chemical formula 21, and
Y is a hydrogen atom, the following chemical formula 20, or the following chemical formula 21,
(except for a case where both X and Y are hydrogen atoms)),

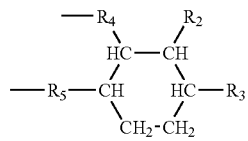
(chemical formula 6)

(wherein $R_2$ and $R_3$ are alkyl groups and $R_4$ and $R_5$ are alkene groups; and the total number of carbon atoms of $R_2$, $R_3$, $R_4$, $R_5$ is 14 to 42),

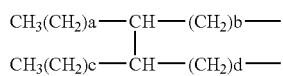
(chemical formula 7)

(wherein a, b, c, and d are each integers such that $16 \leq a+b+c+d \leq 44$);

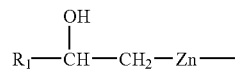
(chemical formula 20)

(wherein $R_1$ is an aliphatic hydrocarbon group having 3 to 22 carbon atoms, Z is the following chemical formula 22 and/or the following chemical formula 23, and n is an integer less than or equal to 38 including zero),

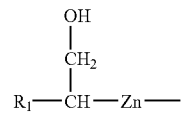
(chemical formula 21)

(wherein $R_1$ is an aliphatic hydrocarbon group having 3 to 22 carbon atoms, Z is the following chemical formula 22 and/or the following chemical formula 23, and n is an integer less than or equal to 38 including zero),

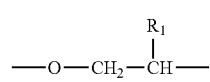
(chemical formula 22)

(wherein $R_1$ is an aliphatic hydrocarbon group having 3 to 22 carbon atoms),

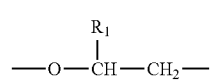
(chemical formula 23)

(wherein $R_1$ is an aliphatic hydrocarbon group having 3 to 22 carbon atoms).

2. A dimer diol derivative obtained by reacting dimer diol with epoxide and represented by the following chemical formula 24,

(chemical formula 24)

(wherein:
R is the following chemical formula 6 or the following chemical formula 7,
X is a hydrogen atom, the following chemical formula 25 or the following chemical formula 26, and
Y is a hydrogen atom, the following chemical formula 25 or the following chemical formula 26
(except for a case where both X and Y are hydrogen atoms)),

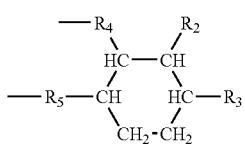
(chemical formula 6)

(wherein $R_2$ and $R_3$ are alkyl groups and $R_4$ and $R_5$ are alkene groups; and the total number of carbon atoms of $R_2$, $R_3$, $R_4$, and $R_5$ is 14 to 42),

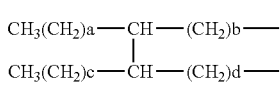
(chemical formula 7)

(wherein a, b, c, and d are each integers such that $16 \leq a+b+c+d \leq 44$);

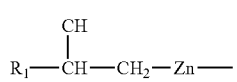
(chemical formula 25)

(wherein $R_1$ is an aliphatic hydrocarbon group having 3 to 22 carbon atoms, Z is the following chemical formula 27 and/or the following chemical formula 28, and n is an integer less than or equal to 38 including zero),

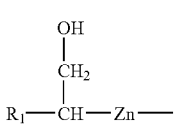
(chemical formula 26)

(wherein $R_1$ is an aliphatic hydrocarbon group having 3 to 22 carbon atoms, Z is the following chemical formula 27 and/or the following chemical formula 28, and n is an integer less than or equal to 38 including zero),

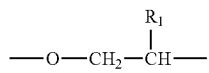

(chemical formula 27)

(wherein $R_1$ is an aliphatic hydrocarbon group having 3 to 22 carbon atoms),

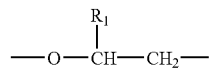

(chemical formula 28)

(wherein $R_1$ is an aliphatic hydrocarbon group having 3 to 22 carbon atoms).

3. The dimer diol derivative according to claim 2 wherein dimer diol is reacted with epoxide in proportion of 1:0.5 to 40 (mol ratio).

4. The dimer diol derivative according to claim 2, wherein the epoxide is at least one selected from 1,2-epoxyhexane, 1,2-epoxyoctane, 1,2-epoxydecane, 1,2-epoxytetradecane, 1,2-epoxydodecane, 1,2-epoxyhexadecane, 1,2-epoxyoctadecane, 1,2-epoxy-5-hexene, 1,2-epoxy-7-octene, 1,2-epoxy-9-decene and 1,2-epoxy-9-hexadecene.

5. The dimer diol derivative according to claim 3, wherein the epoxide is at least one selected from 1,2-epoxyhexane, 1,2-epoxyoctane, 1,2-epoxydecane, 1,2-epoxytetradecane, 1,2-epoxydodecane, 1,2-epoxyhexadecane, 1,2-epoxyoctadecane, 1,2-epoxy-5-hexene, 1,2-epoxy-7-octene, 1,2-epoxy-9-decene and 1,2-epoxy-9-hexadecene.

6. The dimer diol derivative according to claim 1, wherein the dimer diol derivative is part of a cosmetic composition.

7. The dimer diol derivative according to claim 2, wherein the dimer diol derivative is part of a cosmetic composition.

8. The dimer diol derivative according to claim 3, wherein the dimer diol derivative is part of a cosmetic composition.

9. The dimer diol derivative according to claim 4, wherein the dimer diol derivative is part of a cosmetic composition.

* * * * *